United States Patent [19]
Perring et al.

[11] Patent Number: 5,876,755
[45] Date of Patent: Mar. 2, 1999

[54] HUMIDITY RESISTANT COMPOSITION

[75] Inventors: Keith Douglas Perring, Ashford; Richard Arthur Birch, Hythe; Jeremy Nicholas Ness, Canterbury, all of United Kingdom

[73] Assignee: Quest International BV, Naarden, Netherlands

[21] Appl. No.: 507,250

[22] PCT Filed: Feb. 17, 1994

[86] PCT No.: PCT/EP94/00467

§ 371 Date: Sep. 25, 1996

§ 102(e) Date: Sep. 25, 1996

[87] PCT Pub. No.: WO94/19449

PCT Pub. Date: Sep. 1, 1994

[30] Foreign Application Priority Data

Feb. 22, 1993 [EP] European Pat. Off. .............. 93301279
Jun. 18, 1993 [EP] European Pat. Off. .............. 93304801

[51] Int. Cl.[6] ....................................... A61K 9/14
[52] U.S. Cl. .......................... 424/489; 424/401; 424/76.1; 424/70.1; 424/484; 424/486
[58] Field of Search .................................... 424/401, 489, 424/76.1, 70.1, 484, 486

[56] References Cited

U.S. PATENT DOCUMENTS

| 3,681,248 | 8/1972 | Gould et al. | 510/438 |
| 3,821,436 | 6/1974 | Fry | 426/650 |
| 3,868,336 | 2/1975 | Mazzola et al. | 510/433 |
| 4,162,987 | 7/1979 | Maguire | 252/135 |
| 4,417,994 | 11/1983 | Stoddart | 252/135 |
| 5,188,753 | 2/1993 | Schmidt | 252/132 |
| 5,434,069 | 7/1995 | Tsaur | 435/188 |

FOREIGN PATENT DOCUMENTS

2528700  12/1983  France .

*Primary Examiner*—D. Gabrielle Brouillette
*Attorney, Agent, or Firm*—Pillsbury Madison & Sutro LLP

[57] ABSTRACT

Disclosed is a composition comprising a substance encapsulated within a water-sensitive matrix so as to be releasable upon contact with water or aqueous solutions, mixed with particles of inorganic carrier material carrying a poorly water-soluble oil, such that the composition is stable at high relative humidity. Also disclosed are consumer products comprising said compositions and methods for making said compositions.

21 Claims, No Drawings

HUMIDITY RESISTANT COMPOSITION

This application is a 371 of PCT/EA94/00467, filed Feb. 17, 1994, WO94/19449, Sep. 1, 1994.

FIELD OF THE INVENTION

This invention relates to a composition comprising a substance encapsulated within a water-sensitive matrix, which is water-soluble but stable at high relative humidity, and a method of making such a composition.

BACKGROUND OF THE INVENTION

Encapsulated products have been described in which perfume or other poorly water-soluble oil is protected from hostile ingredients by being contained in solid products. Such products are formed by incorporating perfume or other poorly water-soluble oil in a water sensitive matrix which may be a starch or polymer or other material. These encapsulates can also be used to control the release of perfume until the product encounters water; alternatively the perfume may be slowly released by diffusion. The encapsulates may be added to a variety of consumer products, including laundry powder, soap, machinedishwash powder or any other substantially dry solid consumer product. During manufacture or storage these products may encounter high humidity which will cause the breakdown of the encapsulate and the premature release of the perfume.

High humidity conditions are frequently present in a laundry powder factory, particularly those which spray-dry the base powder, but also in non-tower production routes in humid climates. It is not unlikely that the conditions inside a factory could be 33° C./90% relative humidity. Under these conditions a starch encapsulated perfume would be quickly released and the encapsulate powder would become a sticky mass, eventually deliquescing. Thus, it is not normally possible to use starch or similar water soluble encapsulation materials to protect vulnerable perfume ingredients from the hostile materials present in the laundry powder base.

Similarly, very humid conditions are frequently found in soap manufacturing, and in addition soaps may retain a degree of free water within their structure. Thus water sensitive encapsulates are not normally suitable for use in these products.

BRIEF DESCRIPTION OF THE PRIOR ART LITERATURE

Starch encapsulated oils have been prepared and used in a variety of products. Preparation techniques and a range of encapsulation media are described in U.S. Pat. No. 3,455, 838 (NSCC). Starch encapsulates have been used in underarm products to provide controlled release of fragrance (EP 480520, Quest). Starch encapsulation is disclosed in EP 070 719 (Unilever) to provide protection for perfume against the action of various components of the detergent.

Silica loaded with perfume oil has also been described extensively. Zimmermann (GB 1 306 924) found that perfume could be loaded onto silica, up to 2.5 times its own weight, and this remained a free flowing powder. The perfume-loaded powder was added to laundry powder to improve the homogeneity of the perfume addition. The silica used was a finely divided silica gel with a particle size less than 10 $\mu$m.

A similar material was described by Vysoka Skola Chemicko-Technologicka (GB 2 066 839); a porous hydrated silicon dioxide was loaded to 50% with perfume and added to a laundry powder. A substantial reduction of perfume volatility was observed and chemical changes were avoided during storage of the product.

It was found by Colgate Palmolive (GB 2 141 730) that a beneficial effect could be obtained on laundered fabric if perfume were incorporated into the laundry powder via a carrier particle. The carrier particle consisted of zeolite or clay with perfume absorbed or adsorbed onto it at up to 25% of perfume. An additional coating of anionic, nonionic or cationic surfactant was found to improve the deposition of the particle onto the fabric (GB 2 140 820).

Perfumed particles which release perfume when wetted were described by Proctor and Gamble (EP 332 259). In one embodiment, the particles consisted of perfume adsorbed onto silica particles. The silica was preferably fumed silica with a particle size between 0.007 and 2.5 $\mu$m and a surface area of 200 to 400 $m^2$/g. The ratio of perfume to silica in the particles was preferably 0.2:1 to 2.5:1. Lower ratios of perfume to silica were preferable to obtain improved protection of the perfume. These particles were found to be especially useful when incorporated into a fabric softener composition (EP 332 260).

The degree of protection given to perfume in a bleach-containing product by each of the systems is limited. Starch systems are susceptible to breakdown in very humid atmosphere; silica systems do not fully encapsulate perfume but absorb or adsorb it and perfume is relatively free to contact hostile materials in the product. To improve the stability of perfume in the particles they have been coated with various materials. Water soluble encapsulates were prepared by Henkel (DE 2 406 410) with a coating of fatty acid or fatty alcohol which melted above 30° C. These particles protected the embedded materials from attack by atmospheric oxygen, moisture, alkalis or bleaching agents; the particle contents are released in water above 30° C.

In another example (Norda, GB 1 517 124) fragrant urea beads were coated with a mixture of amorphous inorganic adsorbent and dextrin (as a binder). These particles released fragrance gradually over an extend period of time under ambient conditions, and released fragrance rapidly when wetted. The inorganic adsorbent had a surface area of 80 to 400 $m^2$/g and contained a fragrance adsorbed therein.

In a further example (Rhone Poulenc, EP 359 630) a liquid component was contained on sodium sulphate at a loading of 8–12% and the particles mixed with silica at 1–4%. The silica particle size was less than 75 $\mu$m and the silica was not loaded with liquid during processing.

There are also two examples of silica encapsulates prepared with a film of a polymer. In the first (Kokando, JP 55 078 965) perfume was absorbed onto a silica gel (surface area 70–1000 $m^2$/g) and then coated with cyclodextrin. The particles had good perfume retention, storability, combustibility, fumigating properties and fragrancy, and were used in deodorants and insecticides. In the second example (Lion, JP 61 155 307) perfume was absorbed onto silica which was then coated with a water soluble polymer (starch).

Other systems have been described which contain starch encapsulates and also contain silicas as structuring agents in the product. These include Pillsbury (U.S. Pat. No. 3,397, 065) where an edible oil is thickened with silica. Also encapsulated flavour has been added to chewing gum, using silica as a structuring aid (IFF, U.S. Pat. No. 3,920,849). Encapsulated fragrances have been added to fabric softeners and colognes which contained silicas as suspending agent (IFF, U.S. Pat. No. 4,446,032, U.S. Pat. No. 4,428,869). However, in these systems the silica and starch particles are not brought into intimate contact and no interaction between the particles is claimed. Also, no perfume or flavour ingredients were adsorbed or absorbed onto the silica particles during processing.

SUMMARY OF THE INVENTION

In one aspect the invention provides a composition, comprising a substance encapsulated within a water-soluble or water dispersible (hereinafter referred to as "water-sensitive") matrix so as to be releasable upon contact with water or aqueous solutions, mixed with particles of porous inorganic carrier material carrying a poorly water-soluble oil, such that the composition is stable against disintegration of the particles and/or release of the encapsulated substance at high relative humidity.

The encapsulated substance may be any substance which is preferably kept separate from the outside environment and/or from other components in the product to which the encapsulates are added until such time as the encapsulates are dissolved in water and the encapsulated substance is released to perform the function for which it was added. The encapsulated substance may be organic or inorganic in character and may be soluble or insoluble in water. Suitable organic encapsulated substances are poorly water soluble oils (which may be the same as, or different from the oil carried by the inorganic carrier material) and may be for example perfumes, flavours or oily cosmetic ingredients. For the purpose of the present invention an oil is considered poorly water soluble if less than 5 ml of oil is soluble in 95 ml of water at 20° C.

Other suitable encapsulated substances of an inorganic, organic or organometalic character may be bleaching agents, bleach activators or bleach catalysts. Examples of the latter are complexes containing metal ions such as Fe, and in particular Mn, and organic ligands, as are described in EP-A-0 458 397, EP-A-0 458 398 and EP-A-0 509 787. Such complexes may have the formulae:

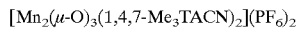

and

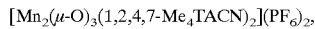

where TACN is 1,4,7-triazacyclononane. These compounds are useful in concentrated washing compositions, thus a composition according to the invention may find particular application in such concentrated washing compositions.

The water-sensitive matrix material may be, for example, starch, modified starch, maltodextrin, cyclodextrin, gums, resins, synthetic or semisynthetic polymers such as polyvinyl pyrrolidine (PVP), polyvinylalcohol (PVA) and cellulose esters, and combinations of these materials. The preferred matrix material comprises modified starch. The encapsulate (i.e. the encapsulated substance within the water-sensitive matrix) is conveniently prepared by spray drying, and is typically particulate so that the composition as a whole is particulate in nature.

The inorganic carrier material used to mix with the encapsulate is preferably a fumed silica, with a particle size of less than 20 nm, such as Aerosol 300™ (Degussa). An additional inorganic carrier material may be mixed with the fumed silica; this may be, for example, a precipitated silica, silica gel or zeolite, preferably with a particle size of less than 20 μm, such as Neosyl GP™ (Crosfield). The weight ratio of fumed silica to additional inorganic material may be between 1:0 and 1:20, preferably 20:1 to 1:4.

The inorganic materials are preferably loaded with poorly water-soluble oil at 0.1–80% w/w, preferably 40–60%.

Suitable poorly water-soluble oils are, for example, perfumes, flavours, moisturisers, emollients or other cosmetic ingredients. The weight ratio of encapsulate to inorganic carrier loaded with poorly water-soluble oil may be in the range 25:1 to 1:25, preferably in the range 1:1 to 1:20, more preferably in the range 1:2 to 1:20.

Compositions in accordance with the invention may be added to solid, substantially dry consumer products, wherein the encapsulated substance will be protected from the action of hostile ingredients in the base, and the encapsulate will be protected from the action of high humidity during manufacture or storage of the product.

The invention thus provides an encapsulate, releasing a perfume or other material when brought in contact with water, mixed with one or more inorganic materials which are loaded with poorly water-soluble oil. The encapsulate can thus be protected from the action of water vapour present in humid atmospheres, with the result that the composition remains free flowing in such conditions, with the encapsulated substance only being released on contact with water or aqueous solutions.

In one embodiment, the composition of the invention is prepared by:

i spray drying the water-sensitive matrix and the substance to be encapsulated so as to form the encapsulate;

ii mixing poorly water-soluble oil with the particles of inorganic carrier material or carrier materials;

iii mixing the oil-laden carrier material or materials with the encapsulate.

When more than one inorganic carrier material is, used, the order of addition of the inorganic carriers to the encapsulate is not critical, but preferably fumed silica is added to the encapsulate after the second inorganic carrier material is added.

To produce an encapsulate containing a poorly water-soluble oil,. such as a perfume, a solution or dispersion of 25–50% w/w, typically 40%, starch (or other water-sensitive matrix) in water is prepared and sufficient perfume or other poorly water soluble oil is added to comprise 15–80% w/w, preferably 20–50%, typically 40%, of the total of starch and encapsulated substance. The emulsion thus obtained is then spray-dried using a conventional spray drying techniques, e.g. a spray-dryer with rotary atomizer, with an inlet temperature above 200° C., typically around 240° C. and an outlet temperature below 120° C., typically 100° C. or below.

On the other hand, if the encapsulated substance is an organometallic complex the quantity thereof in the encapsulate may be as low as 1% w/w of the encapsulate, typically 2.5% w/w or above, and up to 50% w/w.

The silica (or other inorganic carrier) may be agitated in a suitable mixer, e.g. a Tatham Forberg mixer, so as to fluidise the powder and the poorly water-soluble oil, e.g. perfume, sprayed onto the fluidised silica with mixing continued until a homogeneous powder is obtained.

Typically a water releasable encapsulate is charged into a suitable mixer such as a ribbon mixer or a tumble mixer and fumed silica containing poorly water-soluble oil added and mixed to obtain a homogeneous powder. If a second inorganic carrier containing poorly water-soluble oil is to be used it may be added to the mixer before addition of the fumed silica and mixing is also continued to obtain a homogeneous powder.

As used herein the term "perfume" denotes a substantially water-insoluble composition of matter consisting of one or more perfume components, optionally mixed with a suitable solvent of diluent, which is used to impart a desired odour to the product to which it is added and/or to skin, hair or fabric. Perfume components are those constituents of a perfume which are added thereto only or primarily for their olfactive contribution.

Perfume components may be natural products such as essential oils, absolutes, resinoids, resins, concretes, etc., and synthetic perfume components such as hydrocarbons, alcohols, aldehydes, ketones, ethers, acids, esters, acetals, ketals, nitrites, etc., including saturated and unsaturated aliphatic, carbocyclic and heterocyclic compounds. Examples of such perfume components are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, $\alpha$-hexylcinnamaldehyde, 2-methyl-3-(p-tert-butylphenyl) propanal, 2-methyl-3-(p-isopropylphenyl)propanal, 3-(p-tert-butylphenyl)-propanal, tricyclodecenyl acetate, tricyclodecenyl propionate, 4-(4-hydroxy-4-methyl-pentyl)-3-cyclohexenecarbaldehyde, 4-(4-methyl-3-pentenyl)-3-cyclohexenecarbaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, vanillin, eugenol, diphenyl oxide, hydroxycitronellal, ionones, methylionones, isomethylionones, irones, cis-3-hexenol and esters thereof, indan musks tetralin musks isochroman musks macrocyclic ketones, macrolactone musks, ethylene brassylate, aromatic nitromusks.

Suitable solvents and diluents for perfumes as mentioned above are, for example, diethyl phthalate, triethyl citrate, ethanol, isopropanol, dipropylene glycol, etc.

The composition of the invention is suitable for addition to any solid, substantially dry consumer product which is intended to be brought in contact with water, such as laundry powders, soaps, sheet conditioners, non-soap detergent (NSD) bars, talc, rim blocks, carpet shampoos aqueous air fresheners, autodishwash powders, deodorants. For dry powder products (laundry powder, talc, carpet shampoos, aqueous airfreshener, autodishwash powder, deodorant) the composition may be blended into the powder product at an appropriate stage of manufacture. Other products (sheet conditioners, NSD bars) are mixed as hot liquids, the composition may be added to these liquids at less than 80° C. The composition may be added to give a total concentration in the product of encapsulated substance, and poorly water-soluble oil within or on the inorganic carrier, of between 0.01% and 10% w/w of the product. When the encapsulated substance is an organometallic complex, the quantity of the total composition to be added to the product may be such as to cause the quantity of organometallic complex in the product to be as low as 0.001% w/w. In addition to the composition of the invention, free perfume, flavour or cosmetic ingredient may be separately added to the product in a conventional manner.

Composition Stability Test

The composition of the invention is stored in an open glass container for 6 hours at 33° C./90% relative humidity (RH). After this period the composition is inspected visually to assess its flow characteristics. Where a gross change in the flow characteristics is observed relative to the composition prior to storage, the composition is termed 'sticky'. Compositions which remain free-flowing after storage, are inspected microscopically to assess the integrity of the water-releasable encapsulate. If the encapsulate is observed to be entirely intact then the composition is termed 'stable'. However, a slight disintegration visible under the microscope does not necessarily mean that the encapsulated substance is prematurely released to an appreciable extent and may thus be acceptable in many cases.

EXAMPLE 1

A starch encapsulate was prepared containing 40% perfume oil. The starch was a modified waxy maize starch (Capsul™, National Starch & Chemical Corp.) and the perfume was a freshness accord (Fragrance A, formulation below) of perfume components susceptible to attack by bleach components in laundry powder. The encapsulate was prepared by normal spray-drying procedures, well known to those experienced in the art. A solution of 40% w/w of starch in water was prepared and sufficient perfume added to be 40% of the sum total of starch and perfume. This emulsion was then spray-dried using a Niro Mobile Minor with rotary atomizer, inlet temperature 240° C., outlet temperature 100° C.

| Fragrance A | |
|---|---|
| | % w/w |
| Adoxal ™ (Givaudan)[1] | 1.0 |
| Aldehyde C9 50% in DEP (= diethyl phthalate) | 7.0 |
| Aldehyde C10 50% in DEP | 16.0 |
| Aldehyde C11 (undecylenic) 50% in DEP | 30.0 |
| Aldehyde C12 50% in DEP | 10.0 |
| Methyl nonyl acetaldehyde 50% in DEP | 36.0 |

[1]Perfume material supplied by Givaudan-Roure

EXAMPLE 2

A starch encapsulate was prepared, as in example 1, containing 40% w/w of volatile oil (Lemon Californian).

EXAMPLE 3

An encapsulate was prepared, as in example 1, using a mixture of starch (Capsul™) and synthetic polymer (PVA 98.5% mol. hydrolysed, m.wt. 25,000, from Polysciences Inc.) in the ratio 4:1.

EXAMPLE 4

A silica absorbate was prepared containing 50% perfume in silica. The silica was a fumed silica (Aerosol 300™, particle size 7 nm). The perfume was typical of those used in fabric washing powders (Fragrance B, formulation below). The absorbate was prepared by spraying perfume onto the silica in a simple tumble mixer and ageing overnight.

| Fragrance B | |
|---|---|
| | % w/w |
| Anther (Quest)[1] | 1.0 |
| Coumarin | 2.0 |
| Gyrane (Quest) | 0.5 |
| Hexyl-cinnamic aldehyde | 18.0 |
| Jasmacyclene (Quest) | 5.0 |
| Jasmopyrane forte (Quest) | 4.0 |
| Lilial (Givaudan)[2] | 10.0 |
| Lixetone (Quest) | 8.0 |

-continued

| Fragrance B | |
|---|---|
| | % w/w |
| α-Iso-methylionone | 5.0 |
| Para-tert.butyl-cyclohexyl acetate | 5.0 |
| Phenyl-ethyl alcohol | 5.0 |
| Pivacyclene (Quest) | 0.5 |
| Tetrahydrolinalol | 6.0 |
| Traseolide (Quest) | 20.0 |

[1]Perfume material supplied by Quest International
[2]Perfume material supplied by Givaudan-Roure

EXAMPLE 5

A silica absorbate was prepared, as in example 4, containing 50% of a non-odorous oil (isopropyl myristate).

TEST EXAMPLE 6

A silica absorbate was prepared, as in example 4, using a precipitated silica (Neosyl GP™, particle size 18 μm) and containing 50% of a perfume (Fragrance B).

EXAMPLE 7

A silica absorbate was prepared, as in example 6, using a precipitated silica (Neosyl GP™) and containing 50% of a non-odorous oil (isopropyl myristate).

TEST EXAMPLE 8

A series of powder perfumes was prepared by mixing encapsulate of example 1 with absorbates of examples 4 and 6, using a tumble mixer. The mixtures and the relative proportions of the components from examples 1, 4 and 6 in them are listed in Table 1. The samples were stored for 6 hours at 33° C. and 90% RH and examined visually to evaluate the flow characteristics and by microscope to determine the stability of the starch encapsulate under these conditions. The results are shown in Table 1. It can be seen that if, for this system the ratio of fumed silica to precipitated silica is equal to, or greater than 1.7:1 the encapsulates remained entirely unaffected during the storage period.

TABLE 1

Silicas loaded with poorly water-soluble oil

| Sample | Starch encapsulate | Fumed silica absorbate | Precipitated silica absorbate | Ratio of silicas, fumed: precipitated | Encapsulate stability[1] | Flow properties[2] |
|---|---|---|---|---|---|---|
| A | 0.50 | 0.00 | 0.50 | 0.00 | U | S |
| B | 0.50 | 0.50 | 0.00 | ∞ | S | F |
| C | 0.40 | 0.40 | 0.20 | 2.00 | S | F |
| D | 0.40 | 0.20 | 0.40 | 0.50 | U | S |
| E | 0.20 | 0.60 | 0.20 | 3.00 | S | F |
| F | 0.20 | 0.20 | 0.60 | 0.30 | U | F |
| G | 0.05 | 0.90 | 0.05 | 18.00 | S | F |
| H | 0.05 | 0.60 | 0.35 | 1.70 | S | F |
| I | 0.05 | 0.35 | 0.60 | 0.58 | U | F |
| J | 0.05 | 0.05 | 0.90 | 0.06 | U | F |

[1]S = Stable, U = Unstable
[2]F = Free flowing, S = Sticky

EXAMPLE 9

A series of powder perfumes was prepared by mixing encapsulated perfume, as in example 1 with fumed silica and/or precipitated silica, these are listed in Table 2. The samples were then stored for 6 hours at 33° C./90% RH and examined to determine the stability of the starch encapsulate and the flow characteristics of the powder, the results are shown in Table 2. The results show that none of the samples were stable during storage, and that it is necessary of the silica(s) to contain poorly water-soluble oil if they are to protect the starch from the effects of high humidity.

TABLE 2

Silicas not loaded with poorly water-soluble oil

| Sample | Starch encapsulated | Fumed silica | Precipitated silica | Encapsulate stability[1] | Flow properties[2] |
|---|---|---|---|---|---|
| K | 0.50 | 0.00 | 0.50 | U | S |
| L | 0.50 | 0.50 | 0.00 | U | F |
| M | 0.40 | 0.40 | 0.20 | U | F |
| N | 0.40 | 0.20 | 0.40 | U | F |

[1]S = Stable, U = Unstable
[2]F = Free flowing, S = Sticky

EXAMPLE 10

A laundry powder was prepared containing powdered perfume. Powdered perfume as in example 8(E) was added to a laundry powder base (as in U.S. Pat. No. 4,663,068, Example 10) to give a total perfume concentration of 0.6%. The perfume contained in the water sensitive encapsulate was Lemon Californian oil. The odour of the laundry powder was satisfactory and on dissolving in the wash liquor the citrus notes were released.

EXAMPLE 11

A toilet soap was prepared containing powdered perfume. Powdered perfume as in example 8(E) was added to a toilet soap base to give a total perfume concentration of 1.2%. The perfume contained in the silicas (fumed and precipitated) was a floral type, the perfume in the starch encapsulate was fresh/citrus. The fresh soap bar odour was floral but an wetting the bar in-use its odour changed to a fresher, more citrus note.

EXAMPLE 12

A toilet soap was prepared containing powdered perfume as in example 11, except that the silicas (fumed and precipitated) contained a non-odorous oil (isopropyl myristate). The bar had negligible odour when dry, however when wetted in-use a fresh, citrus odour was observed.

We claim:

1. A composition which has been obtained by:
   (a) preparing first particles of an encapsulate comprising a substance which is encapsulated within a water-sensitive matrix, said substance being releasable upon contact with water or aqueous solutions and
   (b) preparing second particles of inorganic carrier material which carry a poorly water-soluble oil, and
   (c) subsequently mixing said first particles and said second particles, said composition being stable at high relative humidity which, in the absence of said second particles results in breakdown of the encapsulate and premature release of the substance.

2. A composition according to claim 1, wherein the substance encapsulated in a water-sensitive matrix comprises a perfume, flavour or cosmetic ingredient.

3. A composition according to claim 1, wherein the substance encapsulated in a water-sensitive matrix comprises an organometallic complex.

4. A composition according to claim 3, wherein the organometallic complex comprises a bleach catalyst.

5. A composition according to claim 4, wherein the organometallic complex has one of the following formulae:

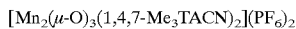

or

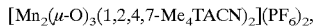

where TACN is 1,4,7-triazacyclononane.

6. A composition according to claim 1, wherein the water-sensitive matrix comprises starch, modified starch, maltodextrin, cyclodextrin, gums, resins, polyvinyl pyrrolidine, polyvinyl alcohol, cellulose esters, or combinations thereof.

7. A composition according to claim 1, wherein an inorganic carrier material is used having a mean particle diameter of less than 20 nm.

8. A composition according to claim 7, wherein the inorganic carrier material comprises fumed silica.

9. A composition according to claim 8 which comprises an additional inorganic carrier material comprising one or more of precipitated silica, silica gel, and zeolite.

10. A composition according to claim 9, wherein the ratio of fumed silica to additional inorganic carrier material is between 1:0 and 1:20.

11. A composition according to claim 1, wherein the substance encapsulated within the water sensitive matrix is also a poorly water-soluble oil and comprises 15–80% w/w of the encapsulate.

12. A composition according to claim 1, wherein the substance encapsulated within the water sensitive matrix is an organometallic complex and comprises 1–50% w/w of the encapsulate.

13. A composition according to claim 1, wherein the particles of inorganic carrier material comprise 0.1–80% w/w poorly water-soluble oil.

14. A composition according to claim 13, wherein the particles of inorganic carrier material comprise 40–60% w/w poorly water-soluble oil.

15. A composition according to claim 1, wherein the ratio of encapsulate to inorganic carrier material is in the range of 25:1 to 1:25.

16. A composition according to claim 15, wherein the ratio of encapsulate to inorganic carrier material is in the range of 1:1 to 1:20.

17. A composition according to claim 1, wherein the encapsulate is stable at 33° C./90% relative humidity.

18. A solid, substantially dry consumer product comprising a composition according to claim 1.

19. A consumer product according to claim 18 wherein the total amount of the substance encapsulated within a water-sensitive matrix and of the poorly water-soluble oil within the organic carrier material is in the range 0.01–10%.

20. A consumer product according to claim 18 selected from the group consisting of laundry powder, talc, autodishwash powder, soap, non-soap detergent bars, sheet conditioners, rim blocks, carpet shampoos, aqueous air fresheners and deodorants.

21. A composition according to claim 1 wherein the composition is stable at 90% relative humidity at 33° C.

* * * * *